United States Patent [19]
Funsten et al.

[11] Patent Number: 5,638,166
[45] Date of Patent: Jun. 10, 1997

[54] APPARATUS AND METHOD FOR RAPID DETECTION OF EXPLOSIVES RESIDUE FROM THE DEFLAGRATION SIGNATURE THEREOF

[75] Inventors: Herbert O. Funsten; David J. McComas, both of Los Alamos, N.M.

[73] Assignee: The Regents of the University of California, Los Alamos, N.M.

[21] Appl. No.: 444,976

[22] Filed: May 18, 1995

[51] Int. Cl.⁶ ............................ G01N 1/00; G01J 3/30
[52] U.S. Cl. .................... 356/36; 356/311; 356/312; 250/554
[58] Field of Search .................... 356/36, 311–312, 356/315; 250/554

[56] References Cited

U.S. PATENT DOCUMENTS

3,644,743  2/1972  Binek et al. ..................... 356/315
3,778,162  12/1973  Gant et al. ..................... 356/312
5,054,914  10/1991  Huber .......................... 356/36

*Primary Examiner*—Georgia Y. Epps
*Assistant Examiner*—Jason D. Eisenberg
*Attorney, Agent, or Firm*—Samuel M. Freund

[57] ABSTRACT

Apparatus and method for rapid detection of explosives residue from the deflagration signature thereof. A property inherent to most explosives is their stickiness, resulting in a strong tendency of explosive particulate to contaminate the environment of a bulk explosive. An apparatus for collection of residue particulate, burning the collected particulate, and measurement of the optical emission produced thereby is described. The present invention can be utilized for real-time screening of personnel, cars, packages, suspected devices, etc., and provides an inexpensive, portable, and noninvasive means for detecting explosives.

7 Claims, 7 Drawing Sheets

APPARATUS AND METHOD FOR RAPID DETECTION OF EXPLOSIVES RESIDUE FROM THE DEFLAGRATION SIGNATURE THEREOF

FIELD OF THE INVENTION

The present invention relates generally to an apparatus for detecting explosives and, more particularly, to an apparatus for the rapid detection and identification of explosive residue from its optical deflagration signature. The invention was made with government support under Contract No. W-7405-ENG-36 awarded by the U.S. Department of Energy to the Regents of The University of California. The government has certain rights in the invention.

BACKGROUND OF THE INVENTION

Explosives are a core component of nuclear, biological, chemical and conventional weapons, as well as of terrorist devices such as car, luggage, and letter bombs. Current methods for detecting the presence of explosives include vapor detection, bulk detection, and tagging. However, these methods have significant difficulties dependent upon the nature of the signature that is detected. See, Fetterolf et al., Portable Instrumentation: New Weapons in the War Against Drugs and Terrorism," *Proc. SPIE* 2092 (1993) 40, Yinon and Zitrin, in *Modern Methods and Applications in Analysis of Explosions*, (Wiley, New York, 1993) Chap. 6; and references therein. Vapor detection is achieved using trained animals, gas chromatography, ion mobility mass spectrometry, and bioluminescence, as examples. All of these techniques suffer from the inherently low vapor pressures of most explosives. Bulk detection of explosives may be performed using x-ray imaging which cannot detect the explosives themselves, but rather detects metallic device components. Another method for bulk detection involves using energetic x-rays to activate nitrogen atoms in the explosives, thereby generating positrons which are detected. This technique requires an x-ray generator and a minimum of several hundred grams of explosives. Bulk detection is also accomplished using thermal neutron activation which requires a source of neutrons and a γ-radiation detector. Thus, bulk detection is not sensitive to trace quantities of explosives and requires large, expensive instrumentation. Tagging requires that all explosives be tagged with, for example, an easily detected vapor. However, since tagging is not mandatory in the United States, this procedure is clearly not reliable. It turns out that there are no technologies for performing accurate, real-time (<6 sec) detection and analysis of trace explosives in situ. Only trained dogs can achieve this goal.

It is known that surfaces in contact with explosives (for example, during storage, handling, or device fabrication) will readily become contaminated with explosive particulates as a result of their inherent stickiness. This phenomenon is illustrated in studies that show large persistence of explosives on hands, even after several washings (J. D. Twibell et al., "Transfer of Nitroglycerine to Hands During Contact with Commercial Explosives," *J. Forensic Science* 27 (1982) 783; J. D. Twibell et al., "The Persistence of Military Explosives on Hands," *J. Forensic Science* 29 (1984) 284). Furthermore, cross contamination in which a secondary surface is contaminated by contact with a contaminated primary surface can also readily occur. For example, a measurable amount of ammonium nitrate (AN) residue has been found on the lease documents for a rental truck, and significant amounts of the explosives PETN (pentaerythritol tetranitrate) and/or AN have been found on clothing and inside vehicles of suspects in two well-publicized bombings. Therefore, explosive residue will likely persist in large amounts on the explosive packaging and environs, as well as on the individuals involved in building the explosive device, which can provide an avenue for detection of the presence of explosives.

Accordingly, it is an object of the present invention to provide a detection and monitoring system capable of quantitatively detecting submicrogram and larger quantities of explosive materials.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims. Key features of useful explosives detectors include high sensitivity and accuracy, substantial specificity, simplicity of operation, reliability, real-time measurement and analysis capability, low cost, and portability.

SUMMARY OF THE INVENTION

To achieve the foregoing and other objects, and in accordance with the purposes of the present invention, as embodied and broadly described herein, the apparatus for determining the presence of particulate from explosive materials hereof may include a light-tight enclosure; means, located within the light-tight enclosure, for heating the particulate to a temperature above the deflagration temperature thereof; and photodetector means located within the light-tight enclosure and disposed such that the optical signature (signal strength, time dependence and perhaps wavelength characteristics) emitted from the particulate as a result of particulate deflagration is detected.

In another aspect of the present invention, in accordance with its objects and purposes, the method for determining the presence of particulate from explosive materials hereof may include the steps of heating the particulate to a temperature above its deflagration temperature and detecting the optical signature emitted from the deflagration of the particulate.

Benefits and advantages of the invention include broad applicability for a wide range of explosives, high specificity and sensitivity for real-time explosive detection.

BRIEF DESCRIPTION OF THE DRAWINGS

The accompanying drawings, which are incorporated in and form a part of the specification, illustrate two embodiments of the present invention and, together with the description, serve to explain the principles of the invention. In the drawings.

DETAILED DESCRIPTION

Briefly, the present invention includes an apparatus and method for detecting and monitoring explosive residue by utilizing its characteristic deflagration (burn) signature. Although combustion kinetics can be quite complex, two important properties governing the combustion rate of materials are the mixing of fuel and oxidant, and the reaction kinetics. If a combustion process requires atmospheric oxygen to burn or the kinetics are complex, as is the case for most common materials, then the burn rate is typically slow. Explosives possess high oxygen content resulting from a pre-mix of fuel and oxidant, and, in general, simple, rapid combustion kinetics. These fundamental differences between explosives and nonexplosives can be utilized to differentiate between the two types of materials. The deflagration energy release per explosive molecule ranges from approximately 11 eV for TNT to approximately 21 eV for PETN. Because of the rapid release of energy, a fraction of the energy released upon deflagration is in the form of ultraviolet, visible, and/or infrared light that can be measured and analyzed in order to detect the presence and/or type of explosive. Since the reaction kinetics of explosives are different than nonexplosives, a fingerprint of the explosive may be derived using characteristic optical emissions. Furthermore, since explosives burn more rapidly and therefore hotter than nonexplosives, the continuum (black body) optical radiation spectrum should be extended to shorter wavelengths.

Ignition temperatures for common explosives range from approximately 170° to 300° C. To initiate deflagration of residue particulates, then, particulates must be heated to at least their ignition temperature, which can be achieved, for example, by collecting the particulates and directing them onto a hot surface or by heating the air surrounding the particulates. It is expected that the optical emission from burning particulates will be related to their burn intensity and rate. For explosives, the characteristic emission should be a high-intensity light burst in a short time period. For a nonexplosive, the characteristic emission, if any, should be a low-intensity light emission over a longer time period. Optical emission can be measured using, for example, a photomultiplier tube, charge coupled device (CCD), or photodiode. In comparing signals from the optical emission of burned explosive and nonexplosive particulate for the same magnitude pulse height, the pulse from an explosive is expected to have one or a combination of the following: a narrower width, different line emission, and/or extension of the continuum optical radiation spectrum to shorter wavelengths relative to nonexplosives. These signatures permit the measurement of explosive residues using pulse shape analysis of the optical emission of the burning residue.

Figure 1:
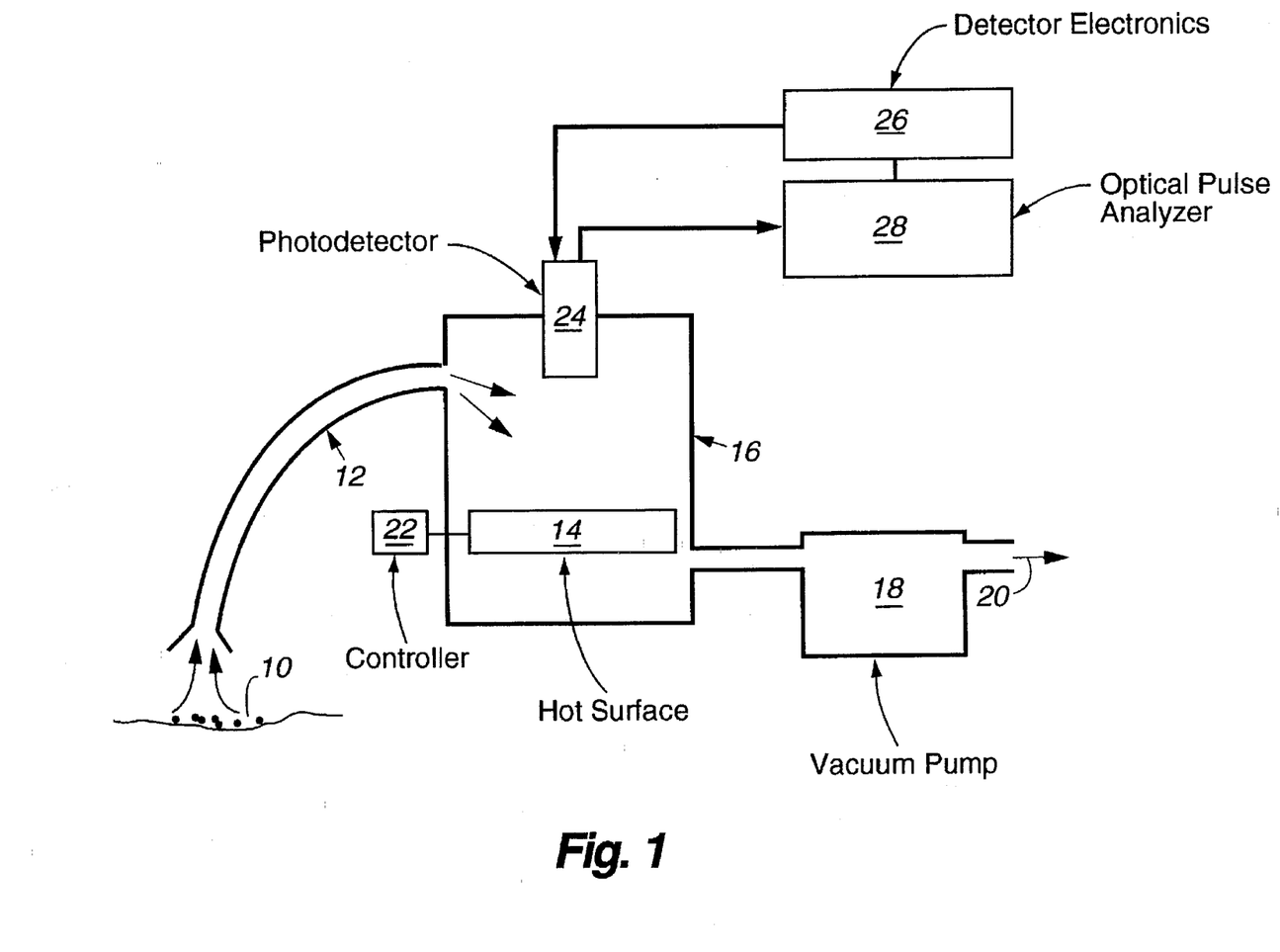
FIG. 1 is a schematic representation of the apparatus of the present invention.

Reference will now be made in detail to the present preferred embodiment of the invention, examples of which are illustrated in the accompanying drawings. Similar or identical structure is identified using identical callouts. Turning now to FIG. 1, where the apparatus of the present invention is schematically illustrated, explosive particulates (and other particulates as well) can be collected by vacuuming or swiping, as examples. Shown are particles, 10, being collected by means of vacuum hose, 12. The particles are caused to flow past hot surface, 14, in light-tight enclosure, 16, by vacuum pump or impeller, 18, which exhausts into the atmosphere, 20. Some of the particles impinge on hot surface, 14. Controller, 22, regulates the temperature of surface, 14, to where particulate deflagration can occur. Photodetector, 24, controlled by detector electronics, 26, receives the optical output of the deflagrating particles which is subsequently analyzed by optical pulse analyzer 28. In manual operation, a sample swipe of residue would be transferred onto hot surface, 14, within enclosure, 16, where deflagration is initiated in the particulates and the resulting optical output is detected and analyzed. It is conceivable that some explosive particles may be attached to nonexplosive dust particulates.

Various other methods for bringing the particulate to their deflagration temperature are also contemplated. Deflagration of the explosive particulate in the sample can also be initiated by using laser or other radiation, or by means of frictional agitation. The temperature at which deflagration occurs can be reduced by increasing the ambient pressure. Suitable photodetectors include, for example, photomultiplier tubes, photodiodes, image intensifier tubes, or CCD detectors. The optical pulse corresponding to the particulate deflagration may be analyzed using the optical signal pulse width, pulse magnitude, continuum spectrum (in part or in whole), or characteristic line emission(s).

Having generally described the invention, the following specific examples are given as further illustration thereof.

EXAMPLE 1

Figure 2:
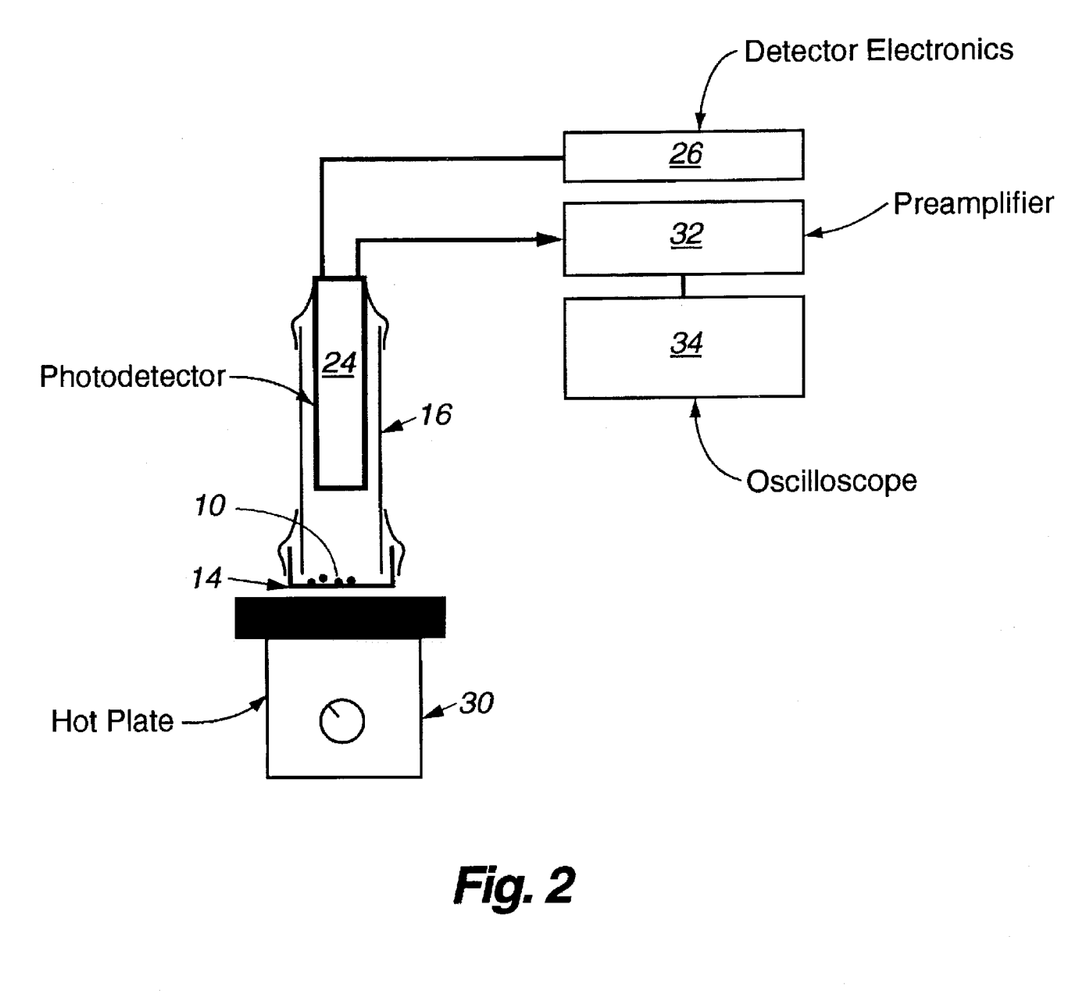
FIG. 2 is a schematic representation of the apparatus used to demonstrate the method of the invention.

FIG. 2, hereof, illustrates the apparatus used in initial experiments for characterizing optical signatures from explosive particulates. Photomultiplier tube (PMT), 24, was mounted on one end of cylindrical enclosure, 16. Sample particulates, 10, were placed in aluminum foil sample cup, 14, which was attached to the other end of enclosure, 16. The apparatus including PMT, 24, enclosure, 16, and sample cup, 14, was made light tight. The PMT was energized using high voltage power supply 26, and cup, 14, was placed in contact with hot plate, 30, such that the sample cup was heated to a temperature of greater than 500° C. (measured using a thermocouple probe, not shown). Within several seconds, explosive particulates were observed to burn, and a photograph was taken of the optical emission pulse as detected by PMT, 24, amplified by preamplifier, 32, and displayed using oscilloscope, 34. In obtaining the data shown in FIGS. 3–7, hereof, it was found that amplification of the optical signal was unnecessary.

Figure 3:
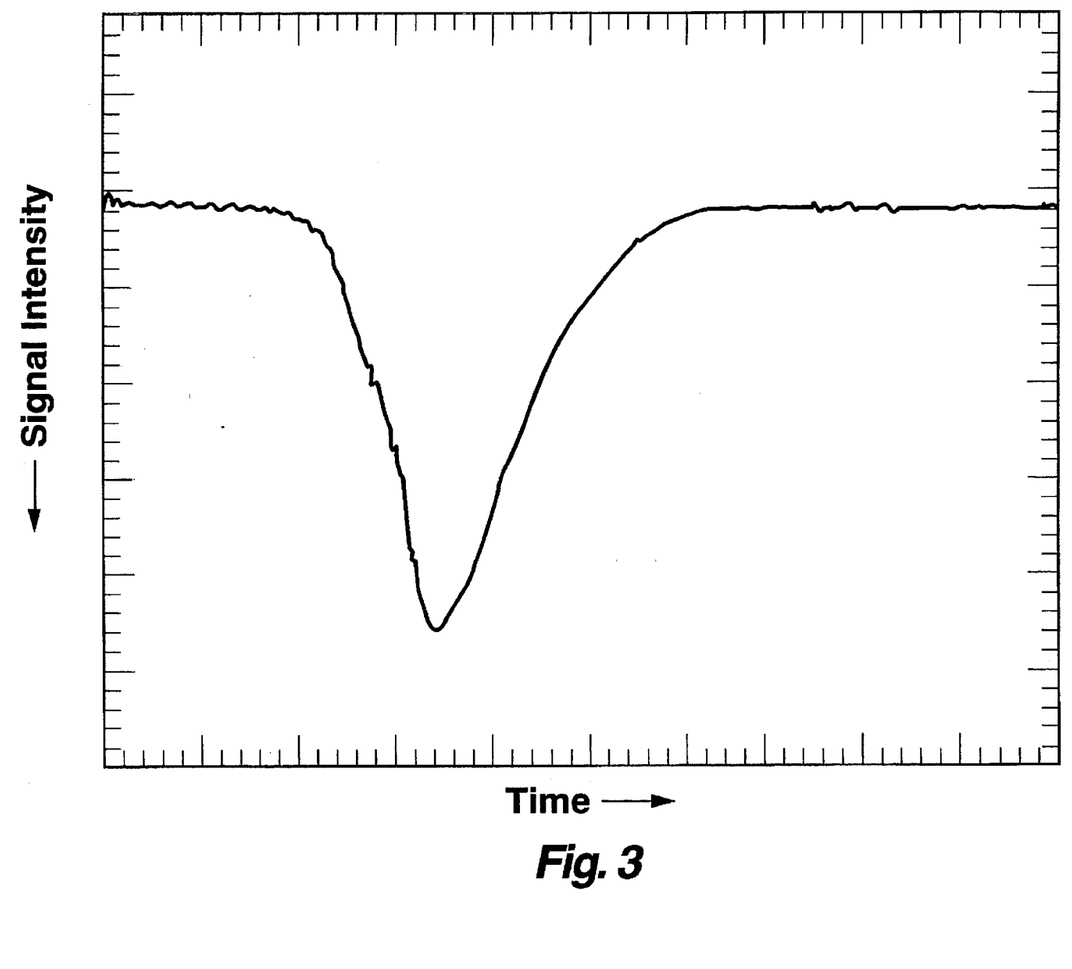
FIG. 3 shows the optical emission signature resulting from the deflagration of a particle of nitrocellulose gunpowder as a function of time.

Individual pellets of nitrocellulose gunpowder were cleaved into particulates having an approximate size $4 \times 10^{-6}$ $cm^3$ (0.2×0.2×0.1 mm) which corresponds to about 7 µg (assuming a density of 1.7 $g/cm^3$). An optical signature was observed within two seconds of contacting the apparatus with the hot plate; this reflected the speed at which the foil bottom of the sample cup was heated from room temperature to a temperature that would ignite the nitrocellulose. FIG. 3 represents a typical optical emission signature of a nitrocellulose particle (approximately 7 µg) that was ignited using a hot plate temperature of approximately 540° C. The (negative-going) pulse magnitude is approximately 0.86V with a full-width-at-half-maximum (FWHM) of approximately 1.5 ms (200 mV per fifth line for the ordinate or signal intensity, and 2 ms per fifth line for the abscissa or time coordinate). One may characterize this pulse using the ratio of the pulse magnitude to the pulse FWHM. Here, this ratio is 0.57V/ms.

EXAMPLE 2

Figure 4:
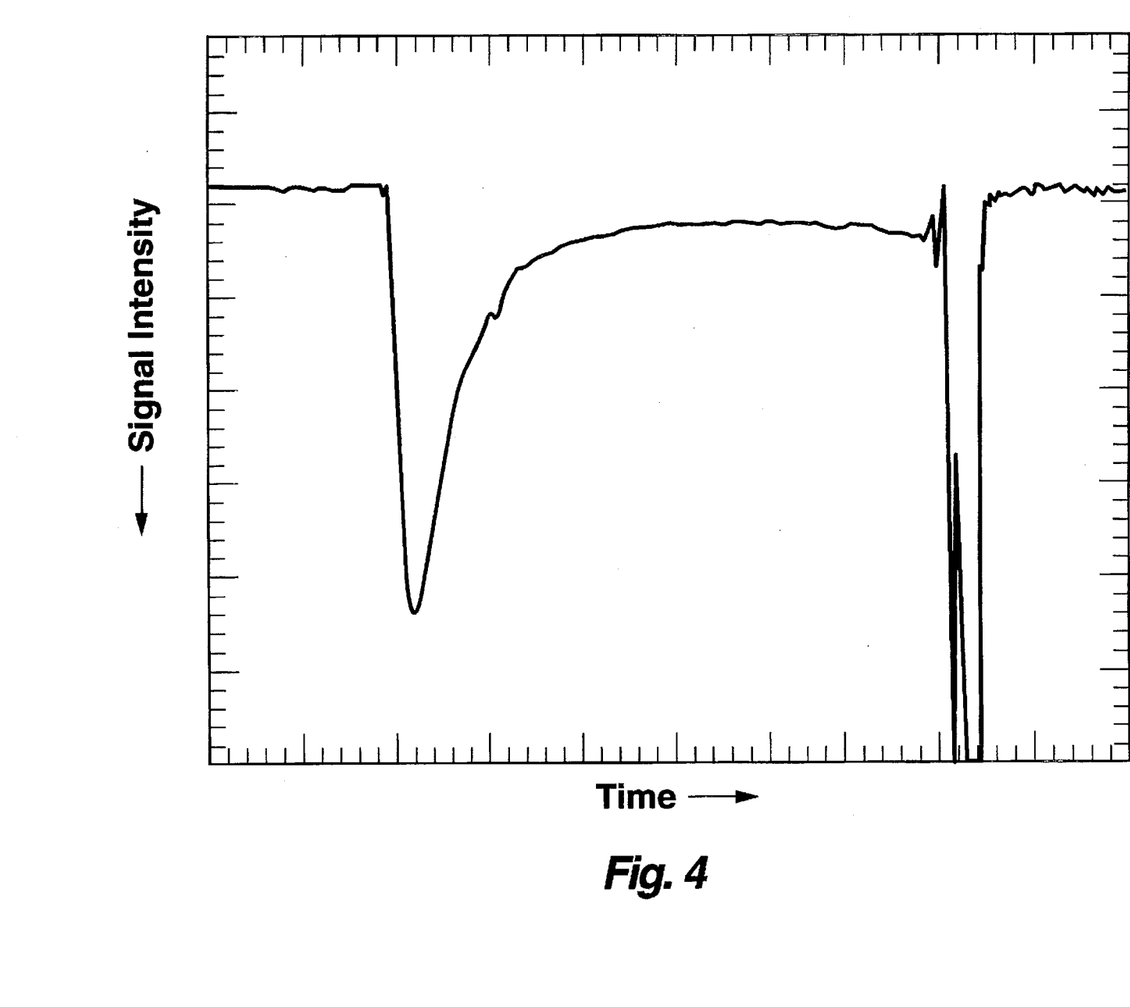
FIG. 4 shows the optical emission signature resulting from the deflagration of a particle from a matchhead as a function of time.

The optical output of matchhead particulates, which are occasionally used in an explosive device, was investigated. FIG. 4 shows the observed optical emission signature from a 0.2×0.2×0.1 mm ($4\times10^{-6}$ cm$^3$ or 6 µg, assuming a density of 1.5 g/cm$^3$) matchhead particle. A double peak with a nonzero emission signature between the peaks was observed in every instance. The first pulse magnitude is approximately 4.5V and the FWHM is approximately 12 ms (1V per fifth line for the signal intensity, and 20 ms per fifth line for the time scale). Here, the ratio of the pulse magnitude to FWHM equals 0.38V/ms which is 33% less than the corresponding ratio for nitrocellulose. Therefore, this ratio permits discrimination between nitrocellulose and match particulates.

EXAMPLE 3

Figure 5:
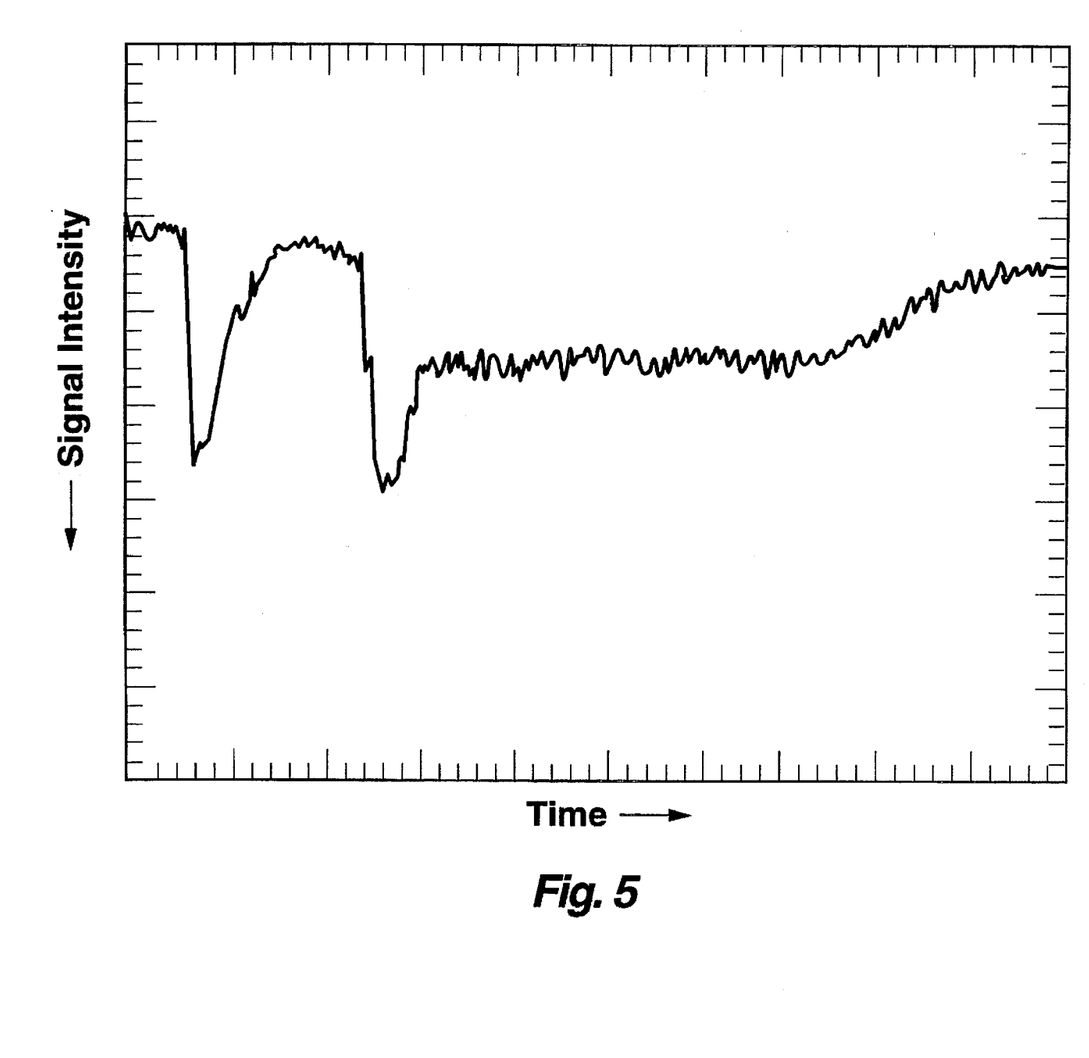
FIG. 5 shows the optical emission signature resulting from the deflagration of a particle of a heavy engine oil as a function of time.

The optical emission signature from the deflagration of Valvoline (type 2050) engine oil, a nonexplosive, is shown in FIG. 5 hereof. The sample size was approximately 1×2× 0.2 mm ($4\times10^{-4}$ cm$^3$ or 400 µg, assuming a density of 1 g/cm$^3$). Two peaks were observed in this sample having a magnitude of approximately 55 mV and a FWHM of 40 ms (20 mV per fifth line signal intensity, and 100 ms per fifth line time scale). For this engine oil sample, the ratio of the pulse magnitude to FWHM equals 0.0014V/ms which is less than 0.3% of the corresponding ratio for nitrocellulose. The two pulses were followed by a 0.7 sec trailing edge having a magnitude of approximately 30 mV. A second sample of engine oil produced a single pulse having a ratio of 0.005 and a 0.6 sec, 30 mV trailing edge.

EXAMPLE 4

Figure 6:
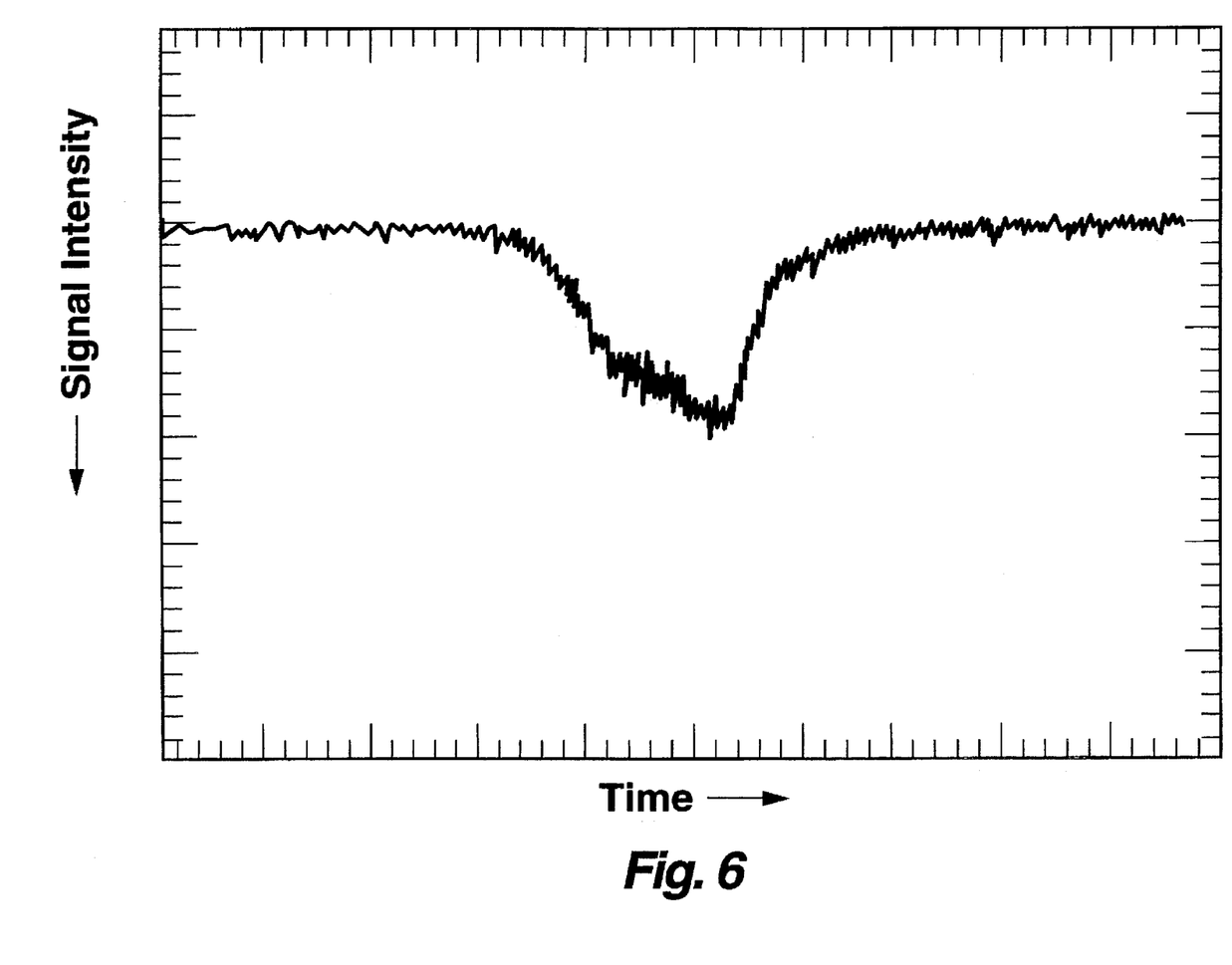
FIG. 6 shows the optical emission signature resulting from the deflagration of a particle of paper as a function of time.

Three types of paper, which are predominantly composed of cellulose and are nonexplosive, were studied by placing the sample cup in contact with the hot plate for 10 to 15 seconds, with no observable optical emission. Subsequent examination indicated heavy charring (the samples turned black). Another sample produced an optical emission as shown in FIG. 6 hereof. The magnitude of the optical emission signature is approximately 9 mV, and the FWHM is approximately 1.5 sec (5 mV per fifth line signal intensity, and 1 s per fifth line time scale). Here, the ratio of the pulse magnitude to FWHM equals $6\times10^{-6}$V/ms which is approximately five orders of magnitude less than that for nitrocellulose. This small ratio is characteristic of the slow burn traits associated with nonexplosive material.

EXAMPLE 5

Figure 7:
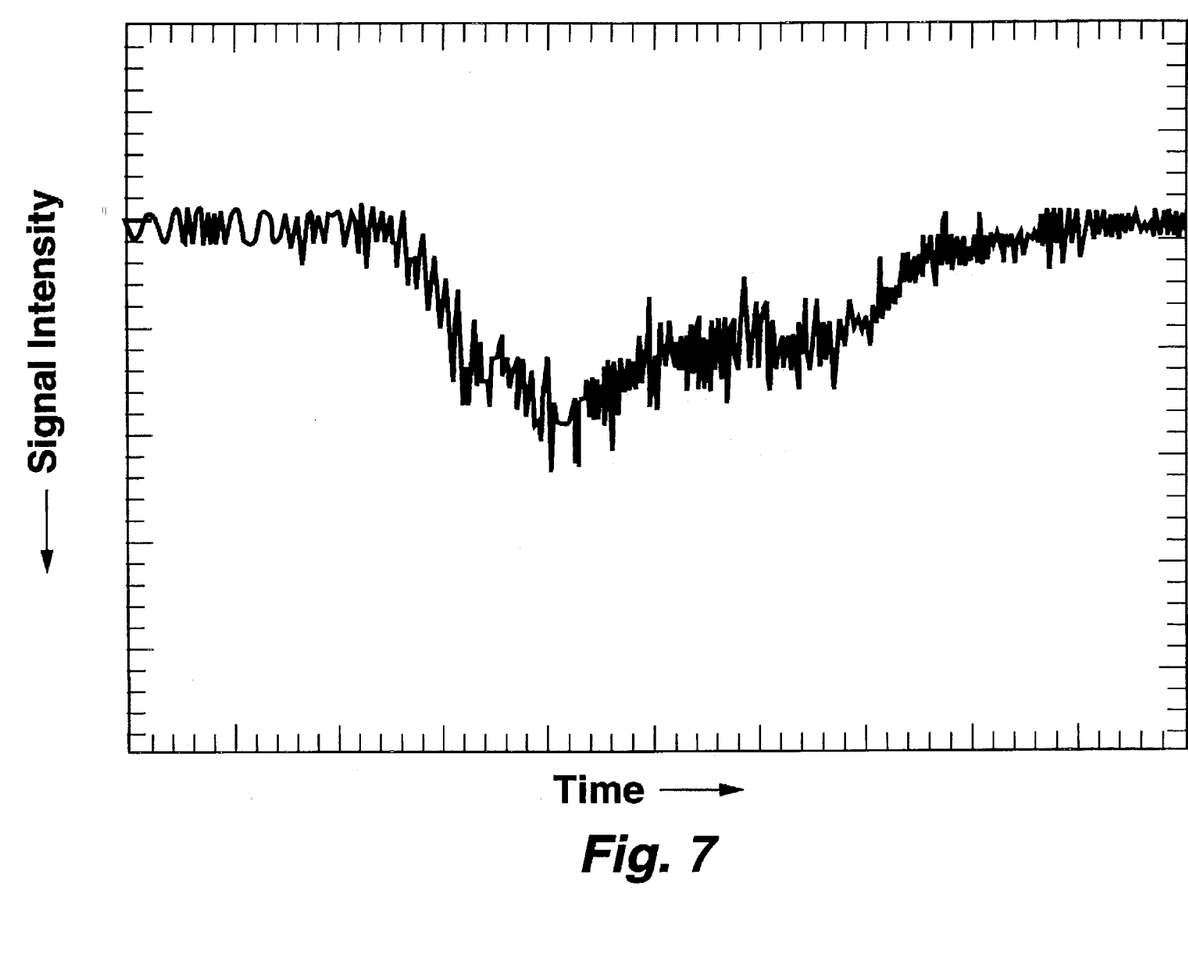
FIG. 7 shows the optical emission signature resulting from the deflagration of a sample of collected room dust as a function of time.

Miscellaneous particulates, including hair, from a vacuum cleaner filter were studied as a representative sample of particulate species and sizes in the environment. The room in which the vacuum cleaner was used had no history of the presence of explosive particulates, so the sample is assumed to contain nonexplosive particulates only. The sample cup was placed in contact with the hot plate for about 15 sec. Only one optical signature was observed which is shown in FIG. 7, hereof. The pulse height was 4 mV and the pulse FWHM was approximately 2 sec (2 mV per fifth line signal intensity, and 1 s per fifth line time scale), yielding a ratio of the pulse magnitude to the FWHM of $2\times10^{-6}$V/ms, indicating that the sample contained nonexplosive material.

EXAMPLE 6

No optical emission was observed from granulated sugar (approximately $6\times10^{-5}$ cm$^3$) after a 15 sec exposure to the hot plate.

These results show that explosive particulates can be uniquely detected and differentiated from nonexplosive material due to their rapid burn signatures. It is expected that different explosive materials can be identified by pulse shape analysis of the observed optical pulse produced by the emitted light upon deflagration. Signatures from explosive materials will be observed as spikes alone or will be observable as spikes on a background of slower burning materials, since most materials either fall into this category or do not burn at all. A high-pass filter could be employed to eliminate signals from background emissions from reaching the recording electronics.

The foregoing description of the invention has been presented for purposes of illustration and description and is not intended to be exhaustive or to limit the invention to the precise form disclosed, and obviously many modifications and variations are possible in light of the above teaching.

The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. An apparatus for determining the presence of particulate from explosive materials, which comprises in combination:

a light-tight enclosure;

a heated surface located within said light-tight enclosure for receiving the particulate and maintained above the deflagration temperature of the particulate, wherein an optical signature is emitted from the deflagration of particulate thereon; and photodetector means located within said light-tight enclosure and disposed such that the emitted optical signature is detected.

2. The apparatus for determining the presence of particulate from explosive materials as described in claim 1, further comprising means for collecting the particulate.

3. The apparatus for determining the presence of particulate from explosive materials as described in claim 2, wherein said means for collecting the particulate comprises means for entraining the particulate in a stream of air, and means for directing the stream of air containing the particulate over said heated surface such that a portion of the particulate impinge thereon.

4. The apparatus for determining the presence of particulate from explosive materials as described in claim 3, wherein said means for entraining the particulate to be investigated in a stream of air, and said means for directing the stream of air containing the particulate over said surface comprise a vacuum pump for evacuating said light-tight enclosure, and tubing means having a first open end located in the vicinity of the particulate to be sampled and a second open end attached to the light-tight enclosure in the vicinity of said heated surface.

5. A method for determining the presence of particulate from explosive materials, which comprises the steps of:

depositing particulate on a surface heated to above the deflagration temperature of the particulate and located within a light-tight enclosure, wherein an optical signature is emitted from the deflagration of the particulate; and detecting the emitted optical signature.

6. An apparatus for determining the presence of particulate from explosive materials, which comprises in combination:

a light-tight enclosure;

means located within said light-tight enclosure for heating the particulate to above the deflagration temperature thereof without direct excitation from flames or plasmas, wherein an optical signature is emitted from the deflagration of the particulate; and photodetector means located within said light-tight enclosure disposed such that the emitted optical signature is detected.

7. A method for determining the presence of particulate from explosive materials, which comprises the steps of:

heating the particulate to above the deflagration temperature thereof without direct excitation from flames or plasmas, within a light-tight enclosure, wherein an optical signature is emitted from the deflagration of the particulate; and detecting the emitted optical signature.

\* \* \* \* \*